United States Patent
Grieshaber

(10) Patent No.: US 8,747,299 B2
(45) Date of Patent: Jun. 10, 2014

(54) METHOD AND DEVICE FOR THE PATHOLOGY ANALYSIS OF THE SCHLEMM'S CANAL

(75) Inventor: Hans R. Grieshaber, Schaffhausen (CH)

(73) Assignee: Grieshaber Ophtalmic Research Foundation, St. Gallen (CH)

( * ) Notice: Subject to any disclaimer, the term of this patent is extended or adjusted under 35 U.S.C. 154(b) by 448 days.

(21) Appl. No.: 13/151,833

(22) Filed: Jun. 2, 2011

(65) Prior Publication Data

US 2012/0310072 A1 Dec. 6, 2012

(51) Int. Cl.
*A61B 1/04* (2006.01)

(52) U.S. Cl.
USPC ............ 600/109; 600/111; 600/160; 600/182; 600/407; 600/476

(58) Field of Classification Search
USPC .......... 600/109, 111, 160, 182, 407, 476–478
See application file for complete search history.

(56) References Cited

U.S. PATENT DOCUMENTS

| | | |
|---|---|---|
| 5,360,398 A | 11/1994 | Grieshaber |
| 5,454,783 A | 10/1995 | Grieshaber |
| 5,676,650 A | 10/1997 | Grieshaber |
| 5,716,328 A | 2/1998 | Grieshaber |
| 5,807,401 A | 9/1998 | Grieshaber |
| 6,149,274 A | 11/2000 | Grieshaber |
| 6,332,866 B1 | 12/2001 | Grieshaber |
| 6,375,642 B1 | 4/2002 | Grieshaber |
| 6,561,974 B1 | 5/2003 | Grieshaber |
| 6,764,439 B2 | 7/2004 | Schaaf et al. |
| 8,034,105 B2 | 10/2011 | Stegmann et al. |
| 2001/0053873 A1 | 12/2001 | Schaaf et al. |
| 2002/0013546 A1 | 1/2002 | Grieshaber |
| 2003/0236484 A1 | 12/2003 | Lynch et al. |
| 2009/0002794 A1 | 1/2009 | Weir et al. |
| 2011/0118649 A1* | 5/2011 | Stegmann et al. ................. 604/8 |
| 2012/0310042 A1* | 12/2012 | Joos et al. ..................... 600/108 |
| 2013/0331760 A1 | 12/2013 | Grieshaber |

* cited by examiner

*Primary Examiner* — Unsu Jung
*Assistant Examiner* — Joel Lamprecht
(74) *Attorney, Agent, or Firm* — Henry M. Feiereisen LLC; Ursula B. Day

(57) ABSTRACT

A method and device are proposed for carrying out ophthalmologic analysis especially for the pathological evaluation of the Schlemm's canal that has been exposed through a scleral flap and into which an micro catheter is inserted that also includes a medium line by which medium is brought into the lumen of the Schlemm's canal for dilating the lumen and a light guide for illumination such that analog images of the dilated lumen, the inner wall of the trabecular tissue and the veins of the aqueous humor can be taken by a camera and transmitted to an outside monitor for visual evaluation.

16 Claims, 3 Drawing Sheets

METHOD AND DEVICE FOR THE PATHOLOGY ANALYSIS OF THE SCHLEMM'S CANAL

The invention refers to a method and a device for carrying out ophthalmologic analyses, in particular for evaluating the pathology of the circular Schlemm's canal which has been exposed by a scleral cut and after lifting up a scleral flap inserting a flexible micro catheter provided with an optical light guide and a line for medium whereby the lumen of the Schlemm's canal is dilated by injecting a fluid and/or gaseous medium.

BACKGROUND OF THE INVENTION

In a healthy eye the drainage of the aqueous humor which circulates in a known fashion from the posterior chamber to the anterior chamber and is drained in the chamber angle via the trabecular tissue into the Schlemm's canal and from there via the episcleral venous system into the blood stream. In pathological conditions of the eye, for example, when the trabecular tissue is clogged due to disease or injury, or when the walls of the Schlemm's canal are conglutinated and/or when the collector channels are clogged, a continuous drainage of the constantly renewing aqueous humor is oftentimes no longer or not sufficiently realized. As a result, the inner pressure of the eye (IOP) can rise to such an extent that the blood circulation of the optical nerves and thereby the function of same is diminished and can thus lead to an eye disease such as glaucoma or "Grüner Star".

PRIOR ART

U.S. publication U.S. 2003/0236484 discloses a device for the treatment of glaucoma which includes a tube-shaped catheter with an injection assembly at a proximal portion and a sleeve disposed at the distal portion, which is insertable with the distal portion through a scleral cut into the lumen of the circular Schlemm's canal. During the circumferential insertion motion of the catheter, a medium is being injected and as a result, the Schlemm's canal in the respective position of the inflated sleeve stretched into a balloon shape.

From publication U.S. Pat. No. 6,74,439 B2 a tube-shaped probe for conducting microsurgical operations is known. The probe has one or more channels and is operatively connected to an endoscope and can be inserted into the anterior chamber of an eye in the direction of the trabecular tissue. In one of the channels an optical light guide for transmitting images of the surgical area is disposed and in a second channel a surgical tool is disposed, wherein the probe is relatively rigid and the surgical tool is operated by an electrical or manual drive and is axially movable in direction of the trabecular tissue

SUMMARY OF THE INVENTION

One aspect of the present invention is to provide a method for an ophthalmologic analysis. Another aspect of the invention is to provide a device to carry out the afore-stated method by which the organic and anatomical structure of the circular Schlemm's canal, in particular the lumen of the Schlemm's canal, can be tested and determined relative to its size and undesirable structures such as septa, as well as the anatomical condition of the trabecular tissue, the veins for the aqueous humor and the number of openings that are connected thereto, and from which conclusion as to their pathology can be drawn from.

The method according to the present invention is characterized in that the dilated lumen of the Schlemm's canal is successively illuminated by the light emitting head of the optical light guide and of the lumen as well as each of the cross sectional size of the expanded lumen and of the inner wall of the trabecular tissue as well as the veins of the aqueous humor for collecting analog data or images and transmitting the images and/or data via a monitor for a visual inspection or for data compilation.

The device according to the present invention for carrying out the method is characterized in that at the distal end of the light guide a light emitting lighting head is disposed for illuminating, starting with the dilated lumen of the Schlemm's canal from the distal end of the inserted micro catheter in an area of at least 0.3 to 0.5 mm radially in all directions and from the distal end in an area of at least 2 mm to 4 mm with light rays oriented in axial direction.

BRIEF DESCRIPTION OF THE DRAWINGS

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
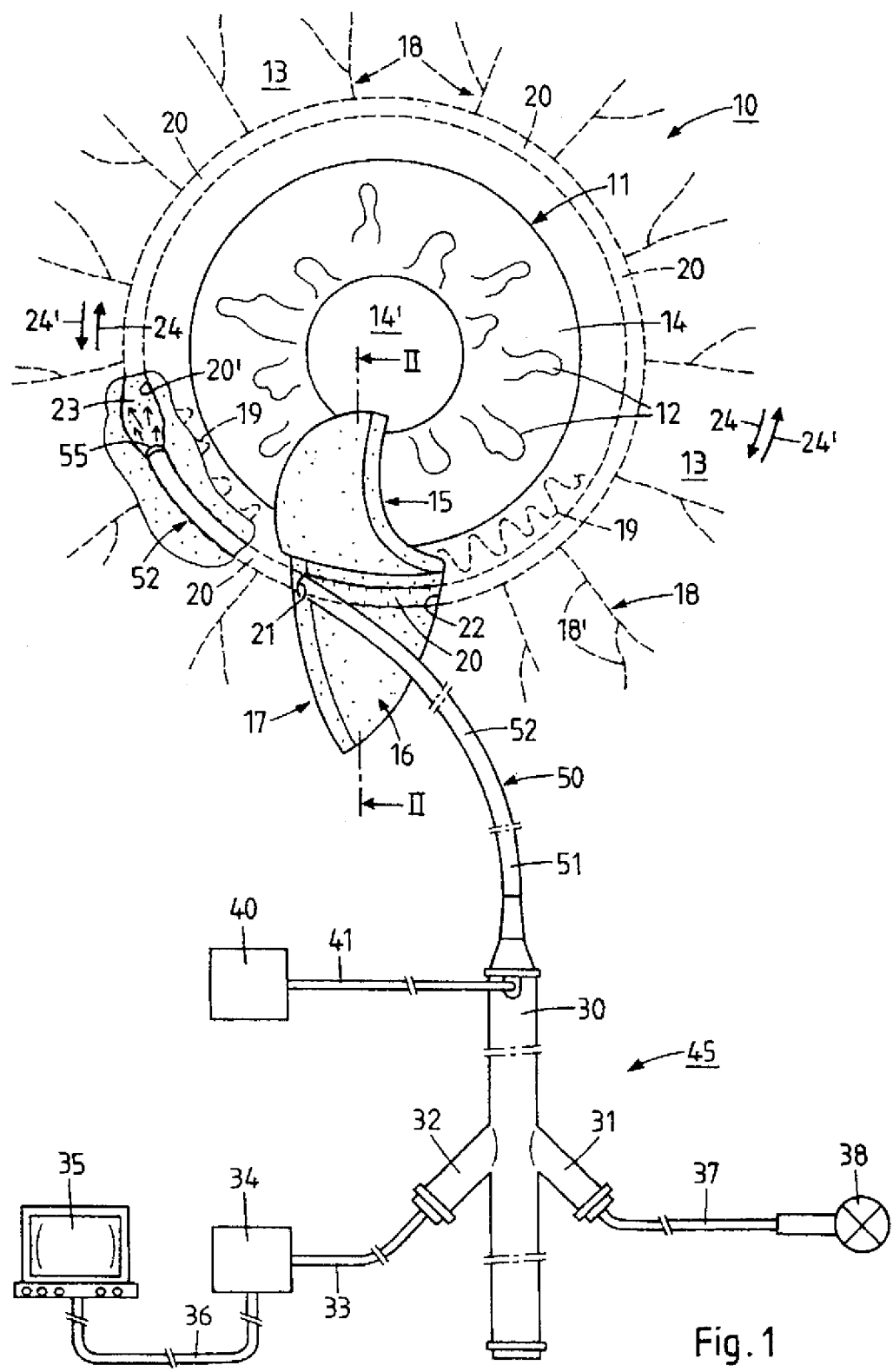
FIG. 1 is a schematic front view of an eye showing a partially exposed Schlemm's canal for the insertion of a micro catheter disposed at an endoscope and operatively connected thereto.

For a better understanding of the problems arising from the pathology analysis and evaluation of the Schlemm's canal, in particular the organic and anatomical condition of the lumen, an eye is schematically shown in FIG. 1 where an incision of the sclera was made for partially exposing the Schlemm's canal in a known manner for the insertion of an elongated micro catheter disposed at an endoscope and in operative connection therewith.

FIG. 1 shows in a schematic illustration of the front section an eye designated as 10 with the cornea 11, the iris 12, the sclera 13, the lens 14 with pupil 14', the trabecular tissue 19 as well as the Schlemm's canal 20 (sinus venosus sclearae) with lumen 23. For the natural drainage of the aqueous humor, which constantly renews itself, the lumen 23 of the Schlemm's canal stands in connection with the circumferentially oriented trabecular tissue 19 as well as each of the openings 18" circumferentially disposed in the Schlemm's canal 20 and small channels of the aqueous humor veins 18 (collector channels).

Further shown in FIG. 1 is the 3 mm×3 mm size incision 17 in the sclera with the opened sclera flap 15 which is kept in open position by means not shown here in detail. The lamellar incision 17 forms scleral bed 16 (reservoir) which is connected to the two oppositely positioned openings 21 and 22 of the Schlemm's canal. After the surgical step, the scleral bed 16 is filled with a highly viscous medium in a known manner, then the scleral flap 15 closed again and sewn together with the sclera 13.

Further shown in FIG. 1 is an endoscope 45, which comprises a housing 30 as well as a proximal portion 51 and a distal portion 52 and a flexible micro catheter 50. At the housing 30 which is for example configured as a handle, a first connection piece 31 and a second connection piece 32 are disposed. A first line 37 connected to a light source 38 is connected at the first connection piece and a second line 33 connected to a video camera 34 is connected at the second connection piece 32. The video camera 34 is connected to a third line 36 with a monitor 35. The endoscope 45 is connected by means of a fourth line 41 to the housing 30 and operatively connected to an irrigation and aspiration unit 40. With the irrigation and aspiration unit 40, a biologically compatible medium, for example, a hydrophilic liquid or a gaseous medium, can be injected into the Schlemm's canal 20 in order to dilate the lumen 23. The micro catheter 50 comprises the proximal portion 51 disposed at the endoscope and the portion 52 disposed at the distal end of the catheter end 55 as shown in the embodiment. In an embodiment not shown here in detail, the distal portion 52 can be removably disposed by means of a coupling to the proximal portion 51 for operative connection with the endoscope 45.

For a pathology analysis and evaluation of the organic and anatomical structure of the Schlemm's canal 20, the distal portion 52 as schematically shown in FIG. 1 is for example inserted through the first opening 21 according to arrow 24 into the lumen 23 of the Schlemm's canal 20. The distal portion 52 is preferably successively introduced by relatively small steps on the order of 1.5 mm to 3 mm. In a targeted irrigation with the liquid or gaseous medium, the lumen 23 is mechanically dilated and thereby any septa removed and aspirated together with any pathological tissue parts that are loosened from the inner wall 20' of the Schlemm's canal.

In the irrigation and aspiration process, the lumen 23 of the Schlemm's canal is first dilated as in the afore-described manner and at the same time or subsequently, the dilated area is lighted by means of a light guide disposed in the micro catheter 50. It is also possible that the Schlemm's canal 20, during the insertion phase of the micro catheter 50, is dilated successively in its circumference and tissue particles and/or cell particles aspirated and in the retracting phase of the micro catheter, the lumen 23 that has already been dilated successively illuminated and the corresponding images and/or data transmitted to monitor 35.

From the illuminated observation area, the condition of the Schlemm's canal 20, in particular, the lumen 23 are examined for anatomical structures in the form of septa or similar, the cross sectional size of the dilated lumen 23 and the inner wall 20' with the trabecular tissue 19 as well as the openings 18" of the aqueous humor veins 18 (collector channels) examined and images and/or data collected through the video camera 34. For example, monographic or stethoscopic images and/or data taken by video camera 34 are transmitted for viewing and evaluation to the monitor 35.

Images and/or data collected by movements comprising successive small steps of 1.0 mm to 3.0 mm in direction of arrow 24 or according to arrow 24' and oriented in circumferential direction of the Schlemm's canal 20 that are analog and reproducibly transmitted to the monitor 35 serve the ophthalmologist in the evaluation of the condition of the Schlemm's canal 20, or in the evaluation of the pathology. Furthermore, the collected results can serve as a basis for further treatment, for example for the insertion of a suitably configured implant into the lumen 23 of the Schlemm's canal 20.

The distal portion 52 of the micro catheter 50 insertable into the Schlemm's canal 20 has a length extending at least from a first circumferential opening 21 up to an opposite second opening 22 in the Schlemm's canal 20. In a preferred embodiment, the length of the micro catheter 50 connected to the endoscope 45 corresponds approximately to 1½ to 2 times of the circular Schlemm's canal.

Figure 2:
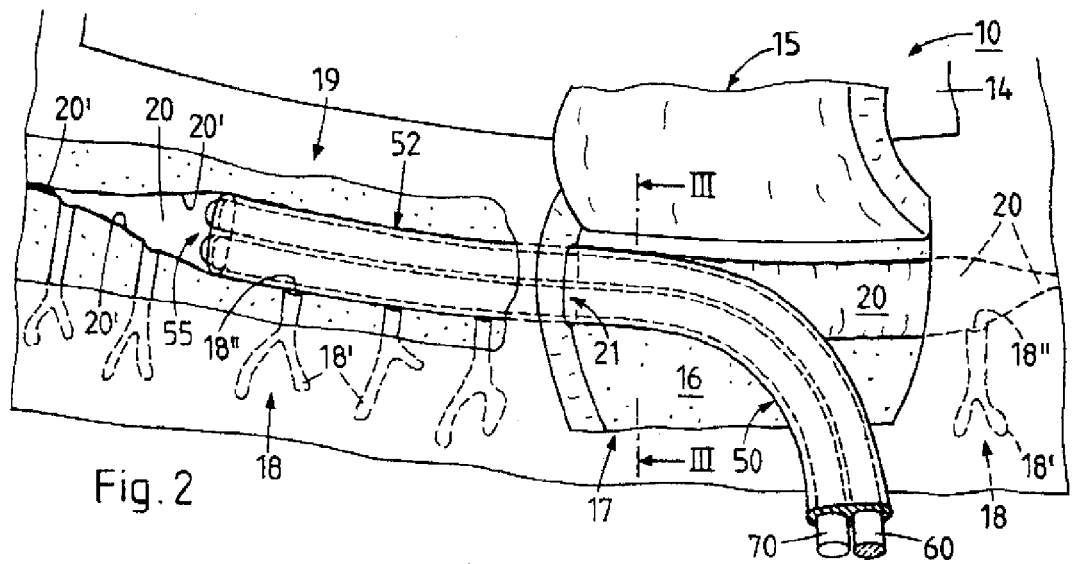
FIG. 2 is an enlarged portion of the eye according to line II-II in FIG. 1 where the distal portion of the micro catheter is inserted into the Schlemm's canal.

FIG. 2 shows in enlarged scale a partial section of the eye 10 with the incision 17 and the scleral bed 16 as well as the opened scleral flap 15. In addition, the distal portion 52 of the micro catheter 50 is shown inserted into the first opening 21 of the Schlemm's canal 20 and provided with a light guide 60 as well as with a tube-shaped irrigation and aspiration line 70. The tube-shaped irrigation and aspiration line 70 is hereinafter called medium line 70. The aqueous humor veins 18 that are in connection with the lumen 23 of the Schlemm's canal 20, with each of the openings 18" and small channels 18' as well as the trabecular tissue 19 are shown schematically. In the area of the distal end 55 of the catheter 50, lumen 23 of the Schlemm's canal 20, due to dilation, is shown partially dilated and shown at a distance from the distal end 55, the partially conglutinated inner walls 20'. The Schlemm's canal 20 in the condition of the pathologically conglutinated (closed) and thus adjoined inner walls 20' is shown here in schematic representation.

Figure 3:
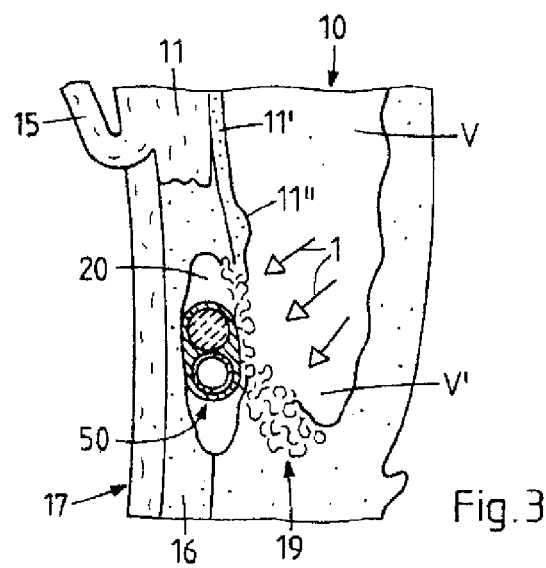
FIG. 3 is a section of a portion of an eye according to line in FIG. 2 where the micro catheter is inserted into the Schlemm's canal.

FIG. 3 shows, according to the line III-III in FIG. 2, a portion of the eye 10 with the anterior chamber V with the chamber angle V', a portion of the cornea 11 with the Descemet membrane 11' and the Schwalb's line 11", as well as the circulation of the aqueous humor according to arrow 1. In addition, the lamellar incision 17 is shown with scleral flap 15 flipped open, as well as the scleral bed 16. In the Schlemm's canal 20 shown schematically in profile cross section, the light guide 60 is for example shown with the tube-shaped medium line 70 and the micro catheter 50 essentially configured as a flat oval.

At this point it is pointed out that the profile cross section of the micro catheter 50 can be configured, for example, as a flat oval or, oval-shaped, elliptical shaped or circular shaped with the channels 54 and 56 disposed separately therein. Furthermore, it is possible that the micro catheter 50 is made from a oval ring-shaped, elliptical ring-shaped or circular ring-shaped tube 58 with an axially extending interior 58'. Preferred embodiments of the micro catheter 50 and the optical light guide 60 as well as the tube-shaped micro catheter 50 and the optical light guide 60 and the tube-shaped medium line 70 are described in the following paragraphs in connection with FIG. 4 to FIG. 8.

Figure 4:
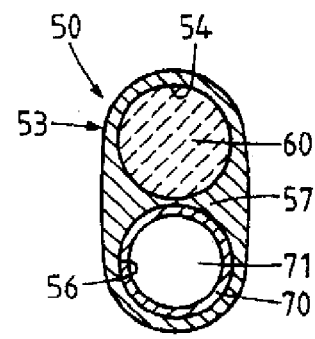
FIG. 4 is the cross section of the profile of a first embodiment of a micro catheter configured as a flat oval and disposed with an optical light guide and an irrigation and aspiration line.

In FIG. 4, for example, the micro catheter 50 is shown enlarged as a flat oval 53 with a first channel 54 and an optical light guide 60 as well as a second channel 56 with a medium line 70 disposed therein. The medium line 70 has an interior 71 oriented in axial direction. The channels 54 and 56 disposed in parallel disposition relative to each other in the elongated flexible micro catheter 50 are separated by in intermediate wall 57 disposed in axial direction to avoid any type interference that might originate from the light guide 60.

Figure 5:
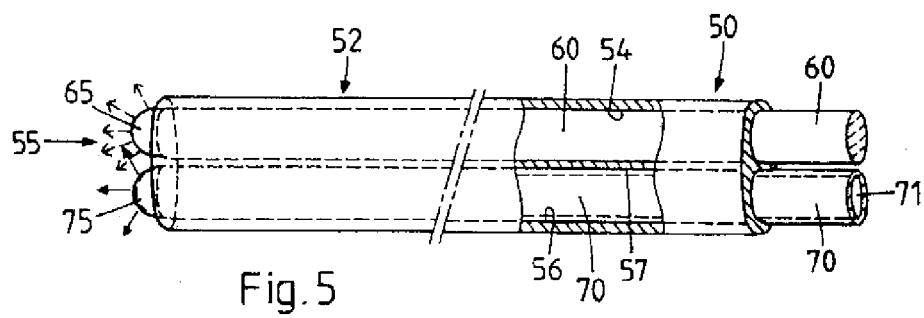
FIG. 5 is a front view and partial section of a second embodiment of the micro catheter with the optical light guide and the irrigation and aspiration line disposed therein.

FIG. 5 shows a partial section of the distal portion 52 of the oval, flat-oval or elliptical shaped micro catheter 50 with the first channel 54 extending in axial direction and the optical light guide 60 disposed therein, as well as the second channel 56 with the medium line 70. The two channels 54 and 56 disposed parallel to each other are separated from each other by a wall 57. The optical light guide 60 at its end is provided with a light head 65; different embodiments of light heads are described in the following paragraphs.

Figure 5A:
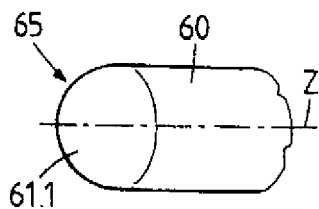
FIG. 5a-5f is a front view of single embodiments of the optical light guide with the light head disposed at the distal end.

In FIGS. 5a to 5f, several embodiments of the light guide having an axis Z with the light heads formed onto the distal end of the light guide are shown in enlarged scale, wherein FIG. 5a shows a first embodiment of the light guide 60 having a light head 65 formed thereon and shaped as a semi-sphere 61.1.

Figure 5B:
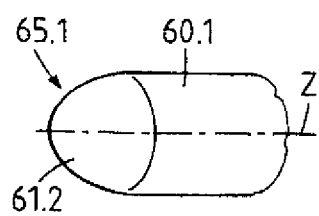
Figure 5C:
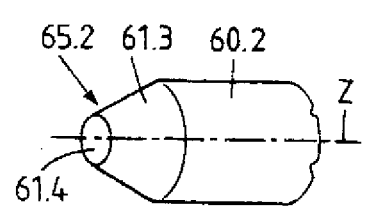

In FIG. 5b, a second embodiment of the optical light guide 60.1 is shown with the parabolic shaped 61.2 light head 65.1, and in FIG. 5c, a third embodiment of the frusto-conical light guide 60.2 is shown with a formed on light head 65.2 provided with a mantle surface 61.3 and a front-side cover surface 61.4.

Figure 5D:
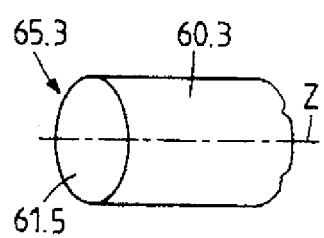

In FIG. 5d, a fourth embodiment of the optical light guide 60.3 is shown with a light head 65.3 disposed thereon and provided with a circular shaped front surface 61.5 oriented perpendicular to the longitudinal axis Z.

Figure 5E:
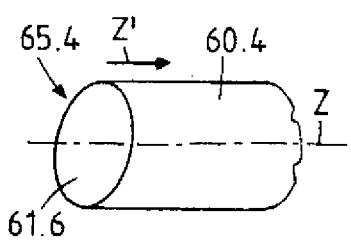
Figure 5F:
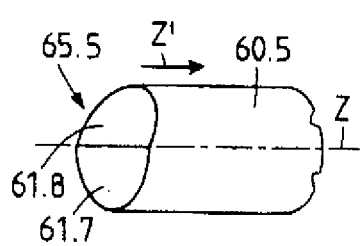

In FIG. 5e, a fifth embodiment of the optical light guide 60.4 is shown with a light head 65.5 disposed thereon and provided with a circular formed front surface 61.6 and backward sloped relative to the longitudinal axis Z in direction of arrow Z', and in FIG. 5f, a further embodiment of the optical light guide 60.5 is shown with the light head 65.5 provided with a semi-circular first front surface 61.7 oriented perpendicular to the longitudinal axis Z, as well as a circular shaped second front surface 61.8 backward sloped relative to the longitudinal axis Z'.

The optical light guides 60-60.5 at each of the distal ends are provided with a ground light head 65-65.5 from which the light rays (viewing angle) are emitted for example, as divergent light rays at a fairly exact emitting angle. The divergent light rays spread radially in all directions which, for example, are emitted from a point-shaped light source. The light intensity of the light rays emitted from the optical light guide 60-60.5 is thereby dependent from the respective emitting angle, whereby in known manner much light is projected onto a small surface with a small emitting angle and less light is projected onto a larger surface with a larger angle. The angle can be in the range from 10 degree to 80 degree.

For the pathology analysis and evaluation and to attain exact reproducibility of the organic and anatomic condition of the Schlemm's canal 20, each of the light heads 65-65.5 has a relatively small light emission angle. The emission angle, not shown here, is for example, on the order of 10 to 80 degree at which the dilated lumen 23 is illuminated directly and exactly at the distal catheter end 55 of the micro catheter 50 and from there images and/or data transmitted to the monitor 35.

The emission angle of each of the light heads 65-65.5 (FIGS. 5a to 5f) is selected such that starting from the distal end of the catheter 55 of the micro catheter 50, the dilated lumen 23 of the Schlemm's canal 20 in the area of about 0.3 mm to 0.5 mm with divergently emitted light rays as well as starting from the distal end of the micro catheter 50 in an area of about 2 mm to 4 mm in axial direction, the inner wall 20' of the Schlemm's canal is sufficiently illuminated for a visual screening of the monitor 35.

Figure 6:
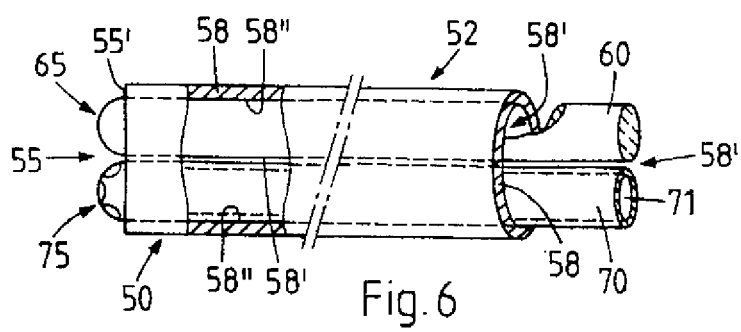
FIG. 6 is a third embodiment of a micro catheter with the optical light guide and the parallel disposed irrigation and aspiration lines extending in axial direction.

FIG. 6 shows as a second embodiment a partial section of the distal portion 52 of the micro catheter 50 constructed from a flexible tube 58 or a hollow needle. The tube 58, for example, in the profile cross section is oval ring-shaped or elliptical ring-shaped and has an axial interior space 58'. In the interior space 58', the light head 65 is disposed and as described in FIG. 5a, is provided with a light guide 60 and a medium line 70, both axially extending in the interior space 58'. At the distal end, the medium line is provided with a head piece 75 for irrigation and aspiration of the medium. The optical light guide 60 and the tube-shaped medium line 70 are disposed axially in parallel disposition and preferably fixed at the facing inner wall 58" of tube 58, with means not shown here in detail. The light head 65 of the light guide 60 as well as the head piece 75 of the medium line 70 are disposed in the flexible tube 58 in such a way that these, relative to the front surface 55', project at a small distance from the distal end of the catheter 55 of tube 58.

Figure 6A:
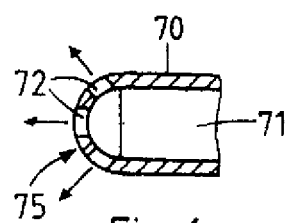
FIG. 6a-6b are enlarged head pieces of the irrigation and aspiration line each configured as a nozzle.

FIG. 6a shows in an enlarged scale, the head piece 75 at the distal end of the medium line 70, which for example is configured as a semi-spherical cap with several bores 72 distributed across the circumference and which are in connection with interior space 71 of the medium line 70. The bores 72 are accordingly for injecting the liquid or gaseous medium or the aspiration of the medium with tissue and cell particles which may have loosened.

Figure 6B:
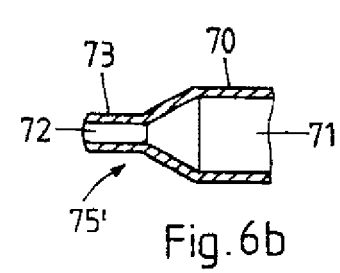

FIG. 6b shows the section of a further embodiment where the head piece 75' disposed at the end of the tube-shaped medium line 70, and starting from the outer diameter of the medium line 70, is configured in the direction of a front tip 73 into conical taper. The tip 73 formed at the head piece 75' is connected to the interior 71 of the tube-shaped medium line 70 via a bore 72 for the injection of a gaseous or liquid medium as well as for the aspiration of the medium together with loose pathological tissue and cell particles. The medium line 70 is operatively connected to irrigation and aspiration unit 40 according to FIG. 1 but not shown in detail.

Figure 7:
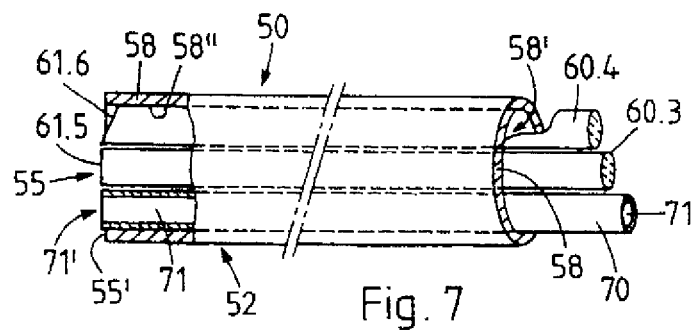
FIG. 7 is a fourth embodiment of the micro catheter with two parallel in axial direction oriented optical light guides and an irrigation and aspiration line disposed parallel thereto.

FIG. 7a is a third embodiment where the flexible micro catheter 50 is shown in an enlarged partial section. The distal portion 52 which consists of a hollow needle or an elongated tube 58 having an oval ring-shaped or an elliptical ring-shaped profile cross section. In the interior 58' of the tube 58 two parallel and axially disposed light guides are shown in this variant, for example the light guides 60.3 and 60.4 as shown in FIG. 5d and FIG. 5e. The optical light guide 60.4 is provided with a circular front face 61.6 which is sloping backward relative to the front face 55' at the distal side in direction to the interior 58' of the elongated tube 58. The light guide 60.3 is provided with circular-shaped front face 61.5, which is flush with the distal front face 55' of tube 58. Parallel to both light guides 60.3 and 60.4, the medium line 70 oriented in axial direction is disposed in the interior 58' of tube 58. The two light guides 60.3 and 60.4 as well as the medium line 70 are preferably fixed, by mean not shown here, at the each of the facing inner wall 58" of tube 58. In the embodiment according to FIG. 7, the medium line 70 differing from the embodiment according to FIG. 6, has a distal opening 71' dimensioned according to the inner diameter.

At this point it should be noted that the micro catheter 50, as for example shown in FIG. 7, can be configured with two light guides axially extending and parallel to each other with the medium line 70 also parallel oriented, whereby the two light guides are provided with two identically constructed light heads or in combination with two differently constructed light heads 65-65.5 according to FIGS. 5a to 5f.

Figure 8:
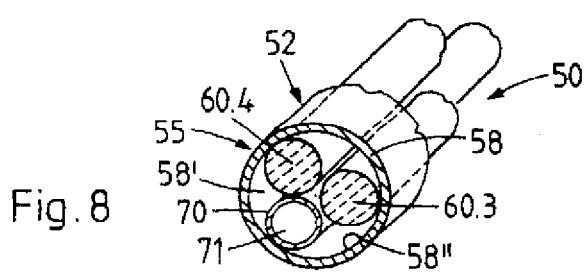
FIG. 8 is a further embodiment of the micro catheter with two parallel in axial direction oriented optical light guides and an irrigation and aspiration line disposed parallel thereto.

In FIG. 8, a further embodiment of the micro catheter 50 is shown as a partial section in an enlarged scale where the distal portion 52 is shown as circular ring-shaped tube 58 or a hollow needle with the axially extending cylindrical interior 58'. In the interior 58', for example are two axially and parallel oriented light guides 60.3 and 60.4 according to FIG. 5d and FIG. 5e. A medium line 70 is also disposed in the interior 58', set off and parallel to the two light guides 60.3 and 60.4. The two light guides 60.3 and 60.4 as well as the medium line 70 is preferably fixed adjacent the inner wall 58" of tube 58 by means not shown here. The front faces of the two light guides 60.3 and 60.4 and the front face of medium line 70 disposed in the tube 58 are preferably ending flush with the front face 55' of the distal catheter end 55.

Ophthalmologic Method steps

As illustrated in FIG. 1, in a first phase, the flexible micro catheter 50 disposed at the endoscope 45 is being inserted with its distal portion 52 through a first opening 21, successively and in small steps of about 1.0 mm to 3 mm into the circular Schlemm's canal 20 and at the same time the gaseous or liquid medium is being injected through the tube-shaped medium line 70 which is operatively connected to a pressure source 40 by means not shown here in detail. The medium which exits at the distal end of the catheter end 55 of the micro catheter 50 from the medium line 70 effects a mechanical dilation successively in circumferential direction of the Schlemm's canal 20, such that subsequently, preferably but simultaneously at each step, the dilated area of the lumen 23 is illuminated by means of the optical light guide 60-60.5.

For an optimal illumination of a dilated Schlemm's canal 20, the single light head 65-65.5 is preferably configured such that starting from the distal catheter end 55 of the micro catheter 50, the dilated lumen 23 of the Schlemm's canal 20 in the area of about 0.3 mm to 0.5 mm is still suitably illuminated by divergently emitted light rays and in axial direction of the Schlemm's canal 20 starting from the inner wall 20' of the catheter end 55 of the micro catheter 50 in the area of about 2 mm to 4 mm for the collection and transmission of analog images and/or data for a visual review at the monitor 35.

As afore-stated, there is further the possibility that in the insertion phase of the micro catheter 50, the Schlemm's canal 20 is first successively dilated in circumferential direction and loosened tissue—and/or cell particles are being aspirated and in the retraction phase of the micro catheter 50 the already dilated lumen 23 is successively illuminated and corresponding images and/or data are being transmitted at the monitor.

From the illuminated observation area, for example the condition of the Schlemm's canal 20, especially the anatomical structures, such as the septa or similar are examined, as well as the size of the cross section of the dilated lumen 23, the inner wall of the trabecular tissue 19 facing the lumen and the number of functional condition of the aqueous humor veins 18 located opposite and their openings 18" examined, and by means of the video camera 34 which is operatively connected to each of the light guides monographic and stereoscopic images and/or data collected. The images and/or data which have been collected through successive movements oriented in the circumference of the Schlemm's canal 20 in the direction of arrow 24 or arrow 24' are transmitted to monitor 35 and then evaluated by the ophthalmologist for judging of the current condition of the Schlemm's canal 20 or the pathology and as a basis for deciding further treatments.

It is furthermore possible that the distal catheter end 55 of the tube-shaped portion 52, for example is produced from reflecting material or provided with a reflecting fluorescent coating so that at a movement according to direction of arrow 24 or 24' in circumferential direction of the Schlemm's canal 20 additionally, the current position of the distal catheter end 55 is visually well recognizable by means of a surgical microscope not shown here.

While the invention has been illustrated and described as embodied in a method and device for the pathology analysis of the Schlemm's canal, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents:

1. A method of ophthalmologic analysis for evaluating the pathology of Schlemm's canal comprising the steps of:
   exposing portion of a lumen of the Schlemm's canal through an opened scleral flap generated by a scleral incision made in an eye,
   inserting into the lumen at least a flexible micro catheter which includes at least one optical light guide and a medium line for supplying a gaseous or liquid medium for dilating the lumen;
   injecting medium through the micro catheter into the lumen of the Schlemm's canal in circumferential direction under pressure to thereby dilate the lumen;
   illuminating the dilated lumen successively with light emitted from a light head of the optical light guide at an angle and collecting analog images and data by means of a camera from each cross section of the dilated lumen, from an inner wall of trabecular tissue and from veins for aqueous humor that are connected to the lumen, and transmitting the images and/or data to an outside monitor.

2. The method of claim 1, wherein in a first phase, dilating the Schlemm's canal successively in circumferential direction and aspirating loosened tissue- and/or cell particles, and in a second phase illuminating the dilated lumen in successive steps by the light head of the optical light guide.

3. The method of claim 2, wherein the successive steps are 1.0 mm to 3.0 mm with divergent light rays from the light head of the optical light guide.

4. The method of claim 1, wherein the dilated lumen of the Schlemm's canal is radially illuminated directly at a distal end of the micro catheter and at a distance of 2 mm to 4 mm in axial direction of the dilated lumen by light emitted from the light head of the optical light guide.

5. The method of claim 1, wherein the dilated lumen is illuminated at an angle of from 10 degree to 80 degree.

6. The method of claim 1, wherein the dilated lumen is illuminated starting from a distal end of the micro catheter in the area of 0.3 mm to 0.5 mm radially in all directions and starting from the distal end of the catheter in the area from 2 mm to 4 mm in axial direction.

7. A device for carrying out ophthalmologic analyses for the evaluation of pathology of the Schlemm's canal comprising:

an endoscope operatively connected a light source, a video camera, a monitor and an irrigation and aspiration unit; wherein a micro catheter is disposed at the endoscope for insertion into a dilated lumen of an exposed section of Schlemm's canal, the micro catheter comprising an axially extending optical light guide housed interior of the micro catheter and in parallel disposition houses a medium line for releasing medium into and aspirating the lumen; wherein a light head is provided at a distal end of the light guide for emission of light to illuminate an area of 0.3 mm to 0.5 mm in radially direction and an area of 2 mm to 4 mm in axial direction of the Schlemm's canal.

8. The device of claim 7, wherein the micro catheter has a profile cross section configured as an oval and wherein the micro catheter includes a first channel for accommodating the light guide and a second channel for accommodating the tube shaped medium line, wherein the two channels are separated by an intermediate wall.

9. The device of claim 7, wherein the micro catheter has a profile cross section of oval, elliptical or circular shape.

10. The device of claim 7, wherein the micro catheter has a profile cross section that is oval ring-shaped, elliptical ring-shaped or circular ring-shaped and an interior extending in axial direction for receiving the light guide and the medium line.

11. The device of claim 10, wherein the light guide with the light head, and the medium line are received in parallel disposition in the micro catheter such that the light head and the medium line end flush with a distal front face of an end of the micro catheter.

12. The device of claim 7, wherein the light emitting light head is configured as a semi-sphere, a parabola, or has a frusto-conical shape.

13. The device of claim 7, wherein the light head is provided with a circular front face oriented perpendicular to a longitudinal axis Z.

14. The device of claim 7, wherein the light head has a circular front face sloping backward relative to a longitudinal axis Z.

15. The device of claim 7, wherein the light head has a semi-circular first front face perpendicular to a longitudinal axis Z and a second semi-circular front face sloping backward relative to the longitudinal axis Z.

16. The device of claim 7, wherein the micro catheter in addition to the medium line comprises two axially extending light guides in parallel disposition, each light guide provided with a light head, wherein the light heads are of identical configuration or are of different configuration.

* * * * *